United States Patent
Kim et al.

(10) Patent No.: US 6,821,768 B2
(45) Date of Patent: Nov. 23, 2004

(54) CORYNEBACTERIUM AMMONIAGENES KCCM 10340 FOR PRODUCING 5'-XANTHYLIC ACID

(75) Inventors: Jeong-Hwan Kim, Seoul (KR);
Young-Hyeon Kwag, Icheon-si (KR);
Jang-Hee Park, Icheon-si (KR);
Eun-Sung Koh, Suwon-si (KR);
Yoon-Suk Oh, Yongin-si (KR);
Jea-Young Chang, Anyang-si (KR);
Kwang-Ho Lee, Anyang-si (KR);
Jae-Ick Sim, Icheon-si (KR);
Jong-Kwon Han, Yongin-si (KR);
Young-Hoon Park, Seongnam-si (KR)

(73) Assignee: CJ Corporation, Seoul (KR)

( * ) Notice: Subject to any disclaimer, the term of this patent is extended or adjusted under 35 U.S.C. 154(b) by 114 days.

(21) Appl. No.: 10/322,455

(22) Filed: Dec. 19, 2002

(65) Prior Publication Data

US 2003/0148498 A1 Aug. 7, 2003

(30) Foreign Application Priority Data

Dec. 28, 2001 (KR) .................................. 10-2001-0086709

(51) Int. Cl.[7] .............................. C12N 1/00; C12N 1/12; C12N 1/20
(52) U.S. Cl. ................. 435/252.1; 435/843; 435/136
(58) Field of Search ................. 435/252.1, 843, 435/136

(56) References Cited

U.S. PATENT DOCUMENTS

2002/0192746 A1 * 12/2002 Takano et al. ............. 435/69.1

FOREIGN PATENT DOCUMENTS

| JP | 60-156399 | 8/1985 |
| JP | 04-262790 | 9/1992 |

OTHER PUBLICATIONS

Teshiba, S. et al; *Production of Nucleotides and Nucleosides by Fermentation*; Gordon and Breach Sci. Pub.; 1989; pp 53–63.

* cited by examiner

*Primary Examiner*—David Naff
*Assistant Examiner*—Deborah K. Ware
(74) *Attorney, Agent, or Firm*—Nath & Associates PLLC; Gary M. Nath; Lee C. Heiman

(57) ABSTRACT

The invention relates to microorganism producing 5'-xanthylic acid.

A 3,4-dehydro-DL-proline resistant *Corynebacterium ammoniagenes* CJXPK001 strain is provided for producing 5'-xanthylic acid. It is a mutant strain of *Corynebacterium ammoniagenes* KFCC 10743 having a lower resistance to 3,4-dehydro-DL-proline. The mutant strain is not affected by osmotic pressure caused by accumulated, highly concentrated solute in a culture medium, and it can produce 5'-xanthylic acid at a high yield and concentration rate.

1 Claim, No Drawings

CORYNEBACTERIUM AMMONIAGENES KCCM 10340 FOR PRODUCING 5'-XANTHYLIC ACID

TECHNICAL FIELD

The invention relates to a microorganism overproducing 5'-xanthylic acid. More specifically, the invention relates to *Corynebacterium ammoniagenes* CJXPK001 which is a mutant strain of *Corynebacterium ammoniagenes* KFCC 10743 having a resistance to 3,4-dehydro-DL-proline.

BACKGROUND ART

Nucleic acid is mostly found in the nucleus of a cell and it includes ingredients such as inosinic acid (inosinate; IMP) and guanylic acid (guanylate; GMP), which have the taste of beef and mushroom respectively.

Since this has been known to the world, and after going through the early stage of extracting small amount of nucleic acid from squids or other fish in order to use it as raw material in food or pharmaceutical sectors, mass production methods were developed. Among those methods to produce the above-mentioned guanylic acid, the use of 5'-xanthylic acid (XMP) is most popular. The above-mentioned 5'-xanthylic acid is an intermediary product of purine nucleotide biosynthesis process and, by means of XMP-glutamine amidotransferase, it is converted into guanylic acid. Therefore the method which produces 5'-xanthylic acid first and converts it into 5'-guanylic acid enzymatically is used in producing 5'-guanylic acid. However in order to mass-produce 5'-guanylic acid, corresponding amount of 5'-xanthylic acid is necessary. Therefore methods to mass-produce 5'-xanthylic acid are underway.

Conventional methods to produce 5'-xanthylic acid are chemosynthesis, deaminization of 5'-guanylic acid which is produced as a result of decomposition of ribonucleic acid in yeast, a method to add xanthine, as precursor material, in fermenting medium, use of a mutant strain of microorganism, a method to add antibiotic material (JP 1477/67 and JP 20390/69), a method to add surfactant (JP 3835/67 and JP 3838/67) and so on. Among these, a direct fermentation method to use a mutant strain of microorganism to produce 5'-xanthylic acid is quite advantageous in terms of industrial aspect. While we developed into the research to produce 5'-xanthylic acid at a large yield rate by using *Corynebacterium ammoniagenes* which is industrially utilized to produce nucleic acids such as inosinic acid and guanylic acid, we were able to, by modifying the existing character of *Corynebacterium ammoniagenes* KFCC 10743, develop a mutant strain with increased productivity of 5'-xanthylic acid and accomplished in this invention.

DISCLOSURE OF THE INVENTION

The purpose of this invention is to procure microorganism capable of producing 5'-xanthylic acid at a large yield rate.

In order to achieve the above-mentioned object, this invention is aimed at providing 3,4-dehydroproline resistant CJXPK001, a mutant strain of *Corynebacterium ammoniagenes* KFCC 10743.

Henceforth the present invention will be explained in more detail.

In order to avoid dehydration by external osmotic pressure, most microorganisms increase their internal osmotic pressure by accumulating organic solute such as ionized potassium and osmolytes in their body. The above-mentioned osmolytes include proline, betaine and carnitine (Beumer, R. R., et al., *Appl. Environ. Microbiol.* 60:1359–1363, 1994), and among them, proline is known as the most important factor in controlling osmotic pressure. Further, in *Brevibacterium lactofermentum*, it is reported that, under increased external osmotic pressure caused by 5'-xanthylic acid outside the bacterial cell, as the activity of pyrroline-5-carboxylate reductase which is an important enzyme in the biosynthetic process increases, proline is accumulated in the bacterial cell (Yoshio K. et al., *Agr. Bio. Chem.*, 53(9): 2475–2479, 1989).

It is also reported that, in case of *E. coli, Salmonella typhimurium, Serratia marcescens* and others, L-proline is accumulated in their cells and it is controlled by external osmotic pressure (V. J. Dunlap et al., *J. Bacteriol.*, 163: 296, 1985).

By providing existing *Corynebacterium ammoniagenes* KFCC 10743 with resistance to L-proline analogue and by suppressing the inhibition of L-proline synthetic process by feedback inhibition, reinforced L-proline synthesis capability was resulted, which further increased osmotic pressure resistant character of microorganism. Finally we were able to develop a mutant strain to produce 5'-xanthylic acid at a large yield rate.

To be more specific, in this innovative research, we adopted *Corynebacterium ammoniagenes* KFCC 10743 as parent strain and treated it with UV radiation and mutation derivatives such as N-methyl-N'-nitro-N-nitrosoguanidine (NTG) according to ordinary procedure and, by adding 0 to 50 mg/L of proline analogue 3,4-dehydroproline (Sigma Company) in the minimum medium shown in the following Table 1, we developed growing mutant strains. From them, a strain which grows in 30 mg/L 3,4-dehydroproline was separated, named CJXPK001. And, it was deposited under the Budapest Treaty to the Korea Culture Center of Microorganisms on Dec. 7, 2001 with accession Number KCCM 10340.

TABLE 1

| Ingredient | Content |
|---|---|
| Glucose | 20 g/L |
| Potassium phosphate monobasic | 1 g/L |
| Potassium phosphate dibasic | 1 g/L |
| Urea | 2 g/L |
| Ammonium sulfate | 3 g/L |
| Magnesium sulfate | 1 g/L |
| Calcium chloride | 100 mg/L |
| Ferrous sulfate | 20 mg/L |
| Manganese sulfate | 10 mg/L |
| Zinc sulfate | 10 mg/L |
| Biotin | 30 ug/L |
| Thiamine hydrochloride | 0.1 mg/L |
| Copper sulfate | 0.8 mg/L |
| Adenine | 20 mg/L |
| Guanine | 20 mg/L |
| pH 7.2 | |

Further, after adding 0 to 50 mg/L of 3,4-dehydroproline in the minimum medium shown in the above Table 1 according to concentration levels, the medium was fermented at 30° C. for 5 days. And the whole process was scrutinized to find the growth rates of the mutant strain CJXPK001 and the parent strain KFCC 10743. The result is shown in the following Table 2.

TABLE 2

| Strain | 3,4-dehydroproline concentration (mg/L) | | | | | | |
|---|---|---|---|---|---|---|---|
| | 0 | 5 | 10 | 20 | 30 | 40 | 50 |
| Parent strain KFCC 10743 | +++ | + | − | − | − | − | − |
| Mutant strain CJXPK001 | +++ | +++ | +++ | ++ | + | − | − |

+: growth, −: no growth

As shown in the above Table 2, the parent strain *Corynebacterium ammoniagenes* KFCC 10743 showed resistance in 5 mg/L of 3,4-dehydroproline of proline analogue but there was no growth observed at the concentration level above 10 mg/L. However the mutant strain CJXK200101 which was obtained in the present invention showed resistance in 3,4-dehydroproline with the concentration level of up to 30 mg/L.

As for the fermentation medium candidates which can be adopted to produce 5'-xanthylic acid with the help of the mutant strain CJXPK001 of the present invention, any medium made of cheap industrial level sugar source material (glucose, fructose and/or other hydrolyzed material of polysaccharide which contains the preceding two), nitrogen source (organic or inorganic), inorganic mineral salt necessary for the growth of microorganisms, rare elements and vitamins will foot the bill.

The present invention will be specifically explained by the following examples.

However the following examples merely give some examples of the present invention and the contents of the present invention are not limited to the following examples.

BEST MODE FOR CARRYING OUT THE INVENTION

EXAMPLE 1

5 mL of seed medium (pH 7.2) made of glucose 30 g/L, peptone 15 g/L, yeast extract 15 g/L, sodium chloride 2.5 g/L, urea 3 g/L, adenine 150 mg/L, guanine 150 mg/L was poured into a test tube having diameter of 18 mm and sterilized. And, after being seeded with the mutant strain CJXPK001 of the present invention, it was cultured with shaking at 180 rpm, 30° C. for 18 hours (seed culture). Then, as fermentation medium, we sterilized separately and concocted A medium (glucose 60 g/L, magnesium sulfate 10 g/L, ferrous sulfate 20 mg/L, zinc sulfate 10 mg/L, manganese sulfate 10 mg/L, adenine 30 mg/L, guanine 30 mg/L, biotin 100 μg/L, copper sulfate 1 mg/L, thiamine hydrochloride 5 mg/L and calcium chloride 10 mg/L, pH 7.2) and B medium (potassium phosphate monobasic 10 g/L, potassium phosphate dibasic 10 g/L, urea 7 g/L and ammonium sulfate 5 g/L). Then they were poured into sterilized 500 mL of Erlenmeyer flask for shaking, 29 mL, 10 mL respectively and 1 mL of the above-mentioned seed medium was seeded and fermented at 200 rpm, 30° C. for 90 hours. Thereafter, the amount of accumulation of 5'-xanthylic acid in the resulted culture medium was measured and it is shown in the following Table 3 (the concentration of accumulated 5'-xanthylic acid is given by 5'-sodium xanthate .7H$_2$O).

COMPARISON EXAMPLE 1

Except for the adoption of parent strain *Corynebacterium ammoniagenes* KFCC 10743, the same method shown in the Example 1 was used in fermenting process and the amount of accumulated 5'-xanthylic acid in the resulted culture medium was measured and shown in the following Table 3.

TABLE 3

| 5'-xanthylic acid amount (g/L) | Mutant strain CJXPK001 | Parent strain KFCC 10743 |
|---|---|---|
| | 26.1 | 23.1 |

As shown in the above Table 3, the produced amount of 5'-xanthylic acid using the mutant strain CJXPK001 (Example 1) of the present invention shows 13% of improvement over the parent strain KFCC 10743 (Comparison Example 1).

EXAMPLE 2

Seed medium 50 mL shown in the Example 1 was poured into 500 mL of Erlenmeyer flask for shaking and sterilized. Then mutant strain CJXPK001 of the present invention was seeded and cultured with shaking at 180 rpm, 30° C. for 24 hours (primary seed culture). After that, secondary seed medium (glucose 60 g/L, potassium phosphate monobasic 2 g/L, potassium phosphate dibasic 2 g/L, magnesium sulfate 1 g/L, ferrous sulfate 22 mg/L, zinc sulfate 15 mg/L, manganese sulfate 10 mg/L, copper sulfate 1 mg/L, calcium chloride 100 mg/L, biotin 150 μg/L, adenine 150 mg/L, guanine 150 mg/L, thiamine hydrochloride 5 mg/L, antifoaming agent 0.6 mL/L, pH 7.2) was poured into 5L experimental fermentation baths (2L each) and sterilized. Then the above primary seed culture of 50 mL was seeded and cultured, with the air supply of 0.5 vvm, at 900 rpm, 31° C. for 24 hours. On culturing, the pH level of the medium was kept at 7.3 with adjusting by ammonia solution (secondary seed culture).

After that, fermentation medium (glucose 151 g/L, phosphoric acid 32 g/L, potassium hydroxide 25 g/L, adenine 198 mg/L, guanine 119 mg/L, ferrous sulfate 60 mg/L, zinc sulfate 42 mg/L, manganese sulfate 15 mg/L, copper sulfate 2.4 mg/L, alaniate 22 mg/L, NCA 7.5 mg/L, biotin 0.4 mg/L, magnesium sulfate 15 g/L, cystinate 30 mg/L, histidinate 30 mg/L, calcium chloride 149 mg/L, thiamine hydrochloride 15 mg/L, antifoaming agent 0.7 mL/L, CSL 27 mL/L, tuna extract 6 g/L, pH 7.3) was poured into 30L experimental fermentation baths (8L each) and sterilized them. Then the above secondary seed culture was seeded into them (1.5L each) and cultured, with the air supply of 1 vvm, at 400 rpm, 33° C. Whenever the residual sugar level drops below 1% during the culturing process, sterilized glucose was supplied and the total sugar level in the fermentation medium was kept at 30%. During the culturing process, the pH level of the medium was kept at 7.3 with ammonia solution and the process took 90 hours. And the amount of accumulated 5'-xanthylic acid in the resulted culture medium was measured and shown in the following Table 4 (the concentration of accumulated 5'-xanthylic acid is given by 5'-sodium xanthate .7H$_2$O).

COMPARISON EXAMPLE 2

Except for the adoption of parent strain *Corynebacterium ammoniagenes* KFCC 10743, the same method shown in the Example 2 was used in fermenting process and the amount of accumulated 5'-xanthylic acid in the resulted culture medium was measured and shown in the following Table 4.

TABLE 4

| 5'-xanthylic acid amount(g/L) | Mutant strain CJXPK0011 | Parent strain KFCC 10743 |
| --- | --- | --- |
| | 143.5 | 124.7 |

As shown in the above Table 4, the produced amount of 5'-xanthylic acid using the mutant strain CJXPK001 of the present invention (Example 2) shows 15.1% of improvement over the parent strain KFCC 10743(Comparison Example 2).

INDUSTRIAL APPLICABILITY

As reviewed so far, Corynebacterium ammoniagenes CJXPK001 of the present invention is resistant to 3,4-dehydro-DL-proline, L-proline analogue, which plays an important role in controlling osmotic pressure. Therefore it is not affected by osmotic pressure caused by accumulated high concentration solute in culture medium and can be used to produce 5'-xanthylic acid at a high yield, concentration rate.

What is claimed is:

1. A biologically pure *Corynebacterium ammoniagenes* CJXPK001 (Accession Number: KCCM 10340) having resistance to 3,4-dehydro-DL-proline in an amount up to 30 mg/L in a culture medium in which said *Corynebacterium ammoniagenes* KCCM 10340 is grown to produce 5'-xanthylic acid, and said *Corynebacterium ammoniagenes* is a mutant strain of *Corynebacterium ammoniagenes* KFCC 10743 having a lower resistance to 3,4-dehydro-DL-proline, and growing in a culture medium containing 3,4-dehydroproline of lower than 30 mg/L concentration and producing 5'-xanthylic acid.

* * * * *